US010175182B2

(12) United States Patent
Xiao et al.

(10) Patent No.: US 10,175,182 B2
(45) Date of Patent: Jan. 8, 2019

(54) CT DETECTION METHOD AND CT DEVICE

(71) Applicants: GRANDPECT COMPANY LIMITED, Beijing (CN); NUCTECH COMPANY LIMITED, Beijing (CN)

(72) Inventors: Yongshun Xiao, Beijing (CN); Zhiqiang Chen, Beijing (CN); Ming Chang, Beijing (CN); Ziran Zhao, Beijing (CN)

(73) Assignees: Grandpect Company Limited, Beijing (CN); Nuctech Company Limited, Beijing (CN)

( * ) Notice: Subject to any disclaimer, the term of this patent is extended or adjusted under 35 U.S.C. 154(b) by 367 days.

(21) Appl. No.: 14/979,259

(22) Filed: Dec. 22, 2015

(65) Prior Publication Data

US 2016/0189403 A1 Jun. 30, 2016

(30) Foreign Application Priority Data

Dec. 31, 2014 (CN) .......................... 2014 1 0851690

(51) Int. Cl.
*G01N 23/00* (2006.01)
*G01N 23/046* (2018.01)
*G06T 11/00* (2006.01)

(52) U.S. Cl.
CPC .......... *G01N 23/046* (2013.01); *G06T 11/005* (2013.01); *G01N 2223/3306* (2013.01); *G06T 2211/421* (2013.01)

(58) Field of Classification Search
CPC ......... G01N 2223/3306; G01N 23/046; G01N 2223/419; G01N 2223/612;

(Continued)

(56) References Cited

U.S. PATENT DOCUMENTS 6,504,892 B1 * 1/2003 Ning .................. G06T 11/006
378/15
7,197,107 B2 * 3/2007 Arai .................... A61B 6/032
378/15

(Continued)

FOREIGN PATENT DOCUMENTS

CN 101396270 A 4/2009
CN 102525527 A 7/2012
(Continued)

OTHER PUBLICATIONS

Zhang et al.; "A Virtual-Focal-Spot-Based Method for High-Resolution Image Reconstruction on X-ray ICT"; China Academic Journal; 2010; p. 332-337 (contains English Abstract).

*Primary Examiner* — Irakli Kiknadze
(74) *Attorney, Agent, or Firm* — Baker & Hostetler LLP (57) ABSTRACT

A CT detection method is provided, comprising the steps of: (1) scanning circumferentially an object to be detected by means of X-ray according to a preset angle sampling value, which represents the number of sampling points in one circle, so as to obtain a group of projection sampling data in different projection angles, the preset angle sampling value being greater than 1000; (2) processing the projection sampling data so as to obtain projection data of a plurality of virtual sub-focuses equivalent to a large focus of radiation source in a CT system; and (3) implementing an image reconstruction according to the projection data of the plurality of virtual sub-focuses.

16 Claims, 3 Drawing Sheets

(58) Field of Classification Search
CPC ......... G01N 2291/0422; G01N 23/083; G01N 29/2481; G01N 29/2487; G01N 29/265; G01N 29/28; G06T 11/005; G06T 2211/421; A61B 6/032; A61B 6/027; A61B 6/4014; A61B 6/03; A61B 6/06; A61B 6/14; A61B 6/4085; A61B 6/466; A61B 6/541; A61B 6/4233; A61B 6/4441; A61B 6/4464; A61B 6/4488; A61B 6/503; A61B 6/5205; A61B 6/542; A61B 6/587; A61B 10/02; A61B 6/547; A61B 6/583; A61B 6/4291; A61B 6/469; A61B 6/487; A61B 6/488; A61B 6/544; A61B 6/548; A61B 6/588; A61B 6/589; A61B 6/025; A61B 6/035; A61B 6/04; A61B 3/0025; A61B 3/102
USPC ..................................... 378/4, 19, 62, 15, 39
See application file for complete search history.

(56) References Cited

U.S. PATENT DOCUMENTS

| | | | |
|---|---|---|---|
| 8,329,522 B2* | 12/2012 | Park | H01L 21/76816 257/204 |
| 9,084,543 B2* | 7/2015 | Kobayashi | A61B 6/032 |
| 2002/0154727 A1* | 10/2002 | Ning | A61B 6/032 378/4 |
| 2011/0188626 A1 | 8/2011 | Moriyoshi et al. | |
| 2012/0177172 A1* | 7/2012 | Ooshima | A61B 6/027 378/4 |
| 2014/0105352 A1 | 4/2014 | Williams | |

FOREIGN PATENT DOCUMENTS

| | | |
|---|---|---|
| CN | 103366389 A | 10/2013 |
| CN | 103913779 A | 7/2014 |
| CN | 104068885 A | 10/2014 |
| CN | 104142353 A | 11/2014 |

* cited by examiner

CT DETECTION METHOD AND CT DEVICE

CROSS-REFERENCE TO RELATED APPLICATION

This application claims the benefit of Chinese Patent Application No. 201410851690.1 filed on Dec. 31, 2014 in the State Intellectual Property Office of China, the whole disclosure of which is incorporated herein by reference.

BACKGROUND OF THE INVENTION

Field of the Invention

The present disclosure relates to a CT detection method and a CT device, and specifically relates to an image reconstruction method in an X-ray CT imaging system.

Description of the Related Art

A CT system is typically used in medical imaging devices and industrial detection arrangements, which scans an object to be detected by means of X-ray, images the object to be detected using scanning data, and thereby detects the interior of the object to be detected. It is necessary for the CT system to have a higher spatial resolution in case that measurement for geometric dimension of the object to be detected and detection for minor detects of the object to be detected are implemented using the CT system.

A patent document CN102525527A discloses a method of processing projection data, which adopts an X-ray computed tomographic device for imaging. The device includes a gantry, which accommodates an X-ray source and a two-dimensional array type X-ray detector. The X-ray source and the two-dimensional array type X-ray detector are installed on a rotating ring in facing opposite sides of a subject to be detected.

According to the method disclosed in the above patent document, the projection data are acquired using a cone beam along a circular trajectory, a weight value for said projection data is determined according to a normalized electrocardiogram gated reconstruction (EGR) weighting function $W_{EGR}(\beta,\gamma)$ based upon an EGR weighting function $U_{EGR}(\Phi(\beta))$, said $U_{EGR}(\Phi(\beta))$ is normalized by a summation of $U_{EGR}(\Phi(\beta^c_n\%))$ from $n=-N_{PI}$ to $n=N_{PI}$, where $\Phi$ is a cardiac phase, $\beta$ is a view angle, $\beta^c_n$ is a complementary view angle, $PI=\pi$; each of the projection data is weighted by said weight value as determined by said $W_{EGR}(\beta,\gamma)$, where $\gamma$ is a fan angle of the cone beam.

However, the spatial resolution of the image obtained by means of the above method cannot meet the requirement for the above-described application.

Actually, spatial resolution is an important parameter for an X-ray CT system, which is limited by some hardware factors including, for example, focus size of a ray source, dimension of a detector, and magnification ratio of a scanning system, and the like.

The scanning system amplification ratio may be chosen based on various system parameters, as well as dimension of the object to be detected, as a result, the focus size of the ray source and the dimension of the detector form factors, which limit the spatial resolution of the system. In addition, in an industrial CT system, since X-ray has relatively high energy, the focus of the ray source is typically sized in a range of 1.0 mm to 2.0 mm, so as to meet the requirement for heat dissipation of target. However, the dimension of the detector unit is of the order of sub-millimeter, accordingly, the focus size of the ray source forms a major factor of limiting the spatial resolution of the CT system.

SUMMARY OF THE INVENTION

To overcome the above problems, there is provided a CT detection method, comprising the steps of (1) scanning circumferentially an object to be detected by means of X-ray according to a preset angle sampling value, which represents the number of sampling points in one circle, so as to obtain a group of projection sampling data in different projection angles, the preset angle sampling value being greater than 1000; (2) processing the projection sampling data so as to obtain projection data of a plurality of virtual sub-focuses equivalent to a large focus of radiation source in a CT system; and (3) implementing an image reconstruction according to the projection data of the plurality of virtual sub-focuses.

In an embodiment of the present invention, the preset angle sampling value is greater than 8000.

In an embodiment of the present invention, the preset angle sampling value N is obtained according to the following formula: $N>2\pi/\tan^{-1}(a/R)$, wherein a is focus size of an X-ray source, R is a distance between the X-ray source and a rotation center of the object to be detected.

In an embodiment of the present invention, in the step (2), the projection data of the plurality of virtual sub-focuses are obtained according to the projection sampling data in different projection angles and an intensity corresponding to the plurality of virtual sub-focuses.

In an embodiment of the present invention, the projection data of the plurality of virtual sub-focuses are obtained using the following formula:

$$q(k,t) = \sum_{i=1}^{M} w(a_i) p_{cir}(\beta_i, t_i)$$

$$\begin{cases} \theta_i = \tan^{-1}(a_i/R) \\ \beta_i = k\dfrac{2\pi}{N} + \theta_i \\ t_i = D[t\cos\theta_i + (D-R)\sin\theta_i]/[R+(D-R)\cos\theta_i - t\sin\theta_i] \end{cases}$$

where D is a distance between the X-ray source and a detector, $a_i$ is a distance of one virtual sub-focus deviating from an ideal point source, M is the number of the virtual sub-focuses, t represents position of the detector, i is a subscript of one virtual sub-focus, $\beta_i$ is projection angular position of one virtual sub-focus, and q(k,t) is an attenuation coefficient of the X-ray, which is obtained from the following formula: $q(k,t) = -\ln[I(k,t)/I_0(t)]$.

In an embodiment of the present invention, before the step (1), the large focus of the CT system is finely divided into the plurality of virtual sub-focuses by means of a focus size measuring method, and the intensity corresponding to the plurality of virtual sub-focuses is obtained.

In an embodiment of the present invention, the step of obtaining the intensity corresponding to the plurality of virtual sub-focuses comprises:

measuring the size of the large focus of the CT system by means of a small hole imaging method;

dividing finely the large focus into the plurality of equivalent virtual sub-focuses; and determining the intensity corresponding to the plurality of equivalent virtual sub-focuses according to a distribution curve of focus intensity.

In an embodiment of the present invention, the method further comprises the step of: correcting the projection sampling data before the step (2).

In an embodiment of the present invention, the step of correcting the projection sampling data comprises:
measuring intensity $I_0(t)$ of the ray attenuated by air;
calculating the attenuation coefficients q(k,t) of the X-ray in different angles using the following formula:

$$q(k,t) = -\ln[I(k,t)/I_0(t)]$$

wherein k is an angle sampling count, which increases from an initial value 1 until the value k is greater than a preset angle sampling count.

There is also provided a CT device, comprising a radiation source, a detector corresponding to the radiation source, a preset angle sampling value determining unit, a projection sampling data processing unit and a reconstruction unit, wherein, the preset angle sampling value determining unit is intended to determine a preset angle sampling value, which represents the number of sampling points in one circle, the preset angle sampling value being greater than 1000; the radiation source and the detector are disposed on either side of an object to be detected, serving as scanning circumferentially the object to be detected by means of X-ray according to the preset angle sampling value, so as to obtain a group of projection sampling data in different projection angles; the projection sampling data processing unit is configured to process the projection sampling data so as to obtain projection data of a plurality of virtual sub-focuses equivalent to a large focus of radiation source in a CT system; and the reconstruction unit is configured to implement an image reconstruction according to the projection data of the plurality of virtual sub-focuses.

In an embodiment of the present invention, the preset angle sampling value is greater than 8000, and the preset angle sampling value N is obtained according to the following formula: $N > 2\pi/\tan^{-1}(a/R)$, wherein a is focus size of an X-ray source, R is a distance between the X-ray source and a rotation center of the object to be detected.

In an embodiment of the present invention, the projection sampling data processing unit obtains the projection data of the plurality of virtual sub-focuses according to the projection sampling data in different projection angles and an intensity corresponding to the plurality of virtual sub-focuses, and the projection data of the plurality of virtual sub-focuses are obtained using the following formula:

$$q(k,t) = \sum_{i=1}^{M} w(a_i) p_{cir}(\beta_i, t_i)$$

$$\begin{cases} \theta_i = \tan^{-1}(a_i/R) \\ \beta_i = k\dfrac{2\pi}{N} + \theta_i \\ t_i = D[t\cos\theta_i + (D-R)\sin\theta_i]/[R + (D-R)\cos\theta_i - t\sin\theta_i] \end{cases}$$

where D is a distance between the X-ray source and the detector, $a_i$ is a distance of one virtual sub-focus deviating from an ideal point source, M is the number of the virtual sub-focuses, t represents position of the detector, i is a subscript of one virtual sub-focus, $\beta_i$ is projection angular position of one virtual sub-focus, and q(k,t) is an attenuation coefficient of the X-ray, which is obtained from the following formula: $q(k,t) = -\ln[I(k,t)/I_0(t)]$.

In an embodiment of the present invention, the device further comprises a focus size measuring unit, a focus dividing unit and an intensity determining unit, wherein, the focus size measuring unit is intended to measure the size of the large focus of the CT system by means of a small hole imaging method; the focus dividing unit is intended to divide finely the large focus into the plurality of equivalent virtual sub-focuses; and the intensity determining unit is intended to determine an intensity corresponding to the plurality of equivalent virtual sub-focuses according to a distribution curve of focus intensity.

In an embodiment of the present invention, the device further comprises a data correction unit for correcting the projection sampling data, wherein,
based on the measured intensity $I_0(t)$ of the ray attenuated by air, attenuation coefficients q(k,t) of the X-ray in different angles are calculated using the following formula:

$$q(k,t) = -\ln[I(k,t)/I_0(t)],$$

wherein k is an angle sampling count, which increases from an initial value 1 until the value k is greater than a preset angle sampling count.

According to the method provided in the present disclosure, it improves the spatial resolution, releases limitation of the focus size of the X-ray source imposing on the spatial resolution, and simplifies scanning mode of the system, thereby achieving a higher ray utilization, higher spatial resolution and higher image reconstruction efficiency.

BRIEF DESCRIPTION OF THE DRAWINGS

To illustrate the technical solutions in embodiments of the present invention or in the prior art more clearly, accompanying drawings for describing the embodiments of the present invention or in the prior art are briefly introduced below. Obviously, the accompanying drawings are only some embodiments of the present invention, and persons of ordinary skill in the art may obtain other drawings from these accompanying drawings without making creative efforts.

DETAILED DESCRIPTION OF PREFERRED EMBODIMENTS OF THE INTENTION

The detailed embodiments of the present invention will be further described in detail below, in combination with the accompanying figures and the examples. The embodiments are merely exemplary, but not to limit the scope of the present invention.

There is provided a CT detection method, comprising the steps of: (1) scanning circumferentially an object to be detected by means of X-ray according to a preset angle sampling value, which represents the number of sampling points in one circle, so as to obtain a group of projection sampling data in different projection angles, the preset angle sampling value being greater than 1000, for example, the value may be 2048, 3072, 4096, 5120, 6144, 7168, etc.; (2) processing the projection sampling data so as to obtain projection data of a plurality of virtual sub-focuses equivalent to a large focus of radiation source in a CT system; and (3) implementing an image reconstruction according to the projection data of the plurality of virtual sub-focuses.

In a preferred embodiment, the preset angle sampling value may be greater than 8000. The preset angle sampling value N is obtained according to the following formula: $N>2\pi/\tan^{-1}(a/R)$, wherein a is focus size of an X-ray source, R is a distance between the X-ray source and a rotation center of the object to be detected. Preferably, in the step (2), the projection data of the plurality of virtual sub-focuses are obtained according to the projection sampling data in different projection angles and an intensity corresponding to the plurality of virtual sub-focuses. This formula also works in the case that the preset angle sampling value is in any other numerical ranges.

In a preferred embodiment, the projection data of the plurality of virtual sub-focuses are obtained using the following formula:

$$q(k, t) = \sum_{i=1}^{M} w(a_i) p_{cir}(\beta_i, t_i)$$

$$\begin{cases} \theta_i = \tan^{-1}(a_i/R) \\ \beta_i = k\dfrac{2\pi}{N} + \theta_i \\ t_i = D[t\cos\theta_i + (D-R)\sin\theta_i]/[R + (D-R)\cos\theta_i - t\sin\theta_i] \end{cases}$$

where D is a distance between the X-ray source and a detector, $a_i$ is a distance of one virtual sub-focus deviating from an ideal point source, M is the number of the virtual sub-focuses, t represents position of the detector, i is a subscript of one virtual sub-focus, $\beta_i$ is projection angular position of one virtual sub-focus, and q(k,t) is an attenuation coefficient of the X-ray, which is obtained from the following formula: $q(k,t)=-\ln[I(k,t)/I_0(t)]$.

Preferably, before the step (1), the large focus of the CT system is finely divided into the plurality of virtual sub-focuses by means of a focus size measuring method, and the intensity corresponding to the plurality of virtual sub-focuses is obtained.

Preferably, the step of obtaining the intensity corresponding to the plurality of virtual sub-focuses comprises: measuring the size of the large focus of the CT system by means of a small hole imaging method; dividing finely the large focus into the plurality of equivalent virtual sub-focuses; and determining the intensity corresponding to the plurality of equivalent virtual sub-focuses according to a distribution curve of focus intensity.

In an embodiment of the present invention, the method further comprises the step of: correcting the projection sampling data before the step (2). Specifically, the step of correcting the projection sampling data comprises:

measuring intensity $I_0(t)$ of the ray attenuated by air;

calculating the attenuation coefficients q(k,t) of the X-ray in different angles using the following formula:

$q(k,t)=-\ln[I(k,t)/I_0(t)]$ wherein k is an angle sampling count, which increases from an initial value 1 until the value k is greater than a preset angle sampling count.

In another embodiment of the present invention, alternatively, the projection data of the plurality of virtual sub-focus may firstly be restored, the data are then corrected, at last, the image reconstruction is implemented.

According to a preferred embodiment of the present invention, there is provided a CT device, comprising a radiation source, a detector corresponding to the radiation source, a preset angle sampling value determining unit, a projection sampling data processing unit and a reconstruction unit, wherein, the preset angle sampling value determining unit is intended to determine a preset angle sampling value, which represents the number of sampling points in one circle, the preset angle sampling value being greater than 1000; the radiation source and the detector are disposed on either side of an object to be detected, serving as scanning circumferentially the object to be detected by means of X-ray according to the preset angle sampling value, so as to obtain a group of projection sampling data in different projection angles; the projection sampling data processing unit is configured to process the projection sampling data so as to obtain projection data of a plurality of virtual sub-focuses equivalent to a large focus of radiation source in a CT system; and the reconstruction unit is configured to implement an image reconstruction according to the projection data of the plurality of virtual sub-focuses.

Preferably, the preset angle sampling value is greater than 8000, and the preset angle sampling value N is obtained according to the following formula: $N>2\pi/\tan^{-1}(a/R)$, wherein a is focus size of an X-ray source, R is a distance between the X-ray source and a rotation center of the object to be detected.

Preferably, the projection sampling data processing unit obtains the projection data of the plurality of virtual sub-focuses according to the projection sampling data in different projection angles and an intensity corresponding to the plurality of virtual sub-focuses, and the projection data of the plurality of virtual sub-focuses are obtained using the following formula:

$$q(k, t) = \sum_{i=1}^{M} w(a_i) p_{cir}(\beta_i, t_i)$$

$$\begin{cases} \theta_i = \tan^{-1}(a_i/R) \\ \beta_i = k\dfrac{2\pi}{N} + \theta_i \\ t_i = D[t\cos\theta_i + (D-R)\sin\theta_i]/[R + (D-R)\cos\theta_i - t\sin\theta_i] \end{cases}$$

where D is a distance between the X-ray source and the detector, $a_i$ is a distance of one virtual sub-focus deviating from an ideal point source, M is the number of the virtual sub-focuses, t represents position of the detector, i is a subscript of one virtual sub-focus, $\beta_i$ is projection angular position of one virtual sub-focus, and q(k,t) is an attenuation coefficient of the X-ray, which is obtained from the following formula: $q(k,t)=-\ln[I(k,t)/I_0(t)]$.

In a preferred embodiment of the present invention, the device further comprises a focus size measuring unit, a focus dividing unit and an intensity determining unit, wherein, the focus size measuring unit is intended to measure the size of the large focus of the CT system by means of a small hole imaging method; the focus dividing unit is intended to divide finely the large focus into the plurality of equivalent virtual sub-focuses; and the intensity determining unit is intended to determine an intensity corresponding to the plurality of equivalent virtual sub-focuses according to a distribution curve of focus intensity.

In a preferred embodiment of the present invention, the device further comprises a data correction unit for correcting the projection sampling data, wherein, based on the measured intensity $I_0(t)$ of the ray attenuated by air, attenuation coefficients q(k,t) of the X-ray in different angles are calculated using the following formula: q(k,t)=−ln [I(k,t)/I$_0$(t)], wherein k is an angle sampling count, which increases from an initial value 1 until the value k is greater than a preset angle sampling count.

The above described embodiments are not intended to limit the present invention, and the person skilled in the art may alter or modify the present invention if desired.

In the following, the embodiments of the present invention are presented to alter the above described embodiments, in which there is provided an image reconstruction method in an X-ray CT imaging system, comprising the steps of:

(1) activating a ray generator and a detector in the X-ray CT imaging system, measuring intensity I$_0$(t) of the ray attenuated by air at position t, and providing the measured data to a data processor in the X-ray CT imaging system;

(2) disposing an object to be detected in the X-ray CT imaging system for scanning, measuring intensity I(k,t) of the ray attenuated by the object to be detected in the current angular position at the position t, and providing the measured data to the data processor in the X-ray CT imaging system, wherein k being an angle sampling count, which increases from an initial value 1 until the value k is greater than a preset angle sampling count;

(3) calculating attenuation coefficients q(k,t) of the X-ray in different angles using the following formula (1):

$$q(k,t)=-\ln [I(k,t)/I_0(t)] \qquad (1)$$

(4) reconstructing a linear attenuation coefficient distribution image of the object to be detected by means of a filtered back projection algorithm based on the data q(k,t) in the step (3).

Figure 1:
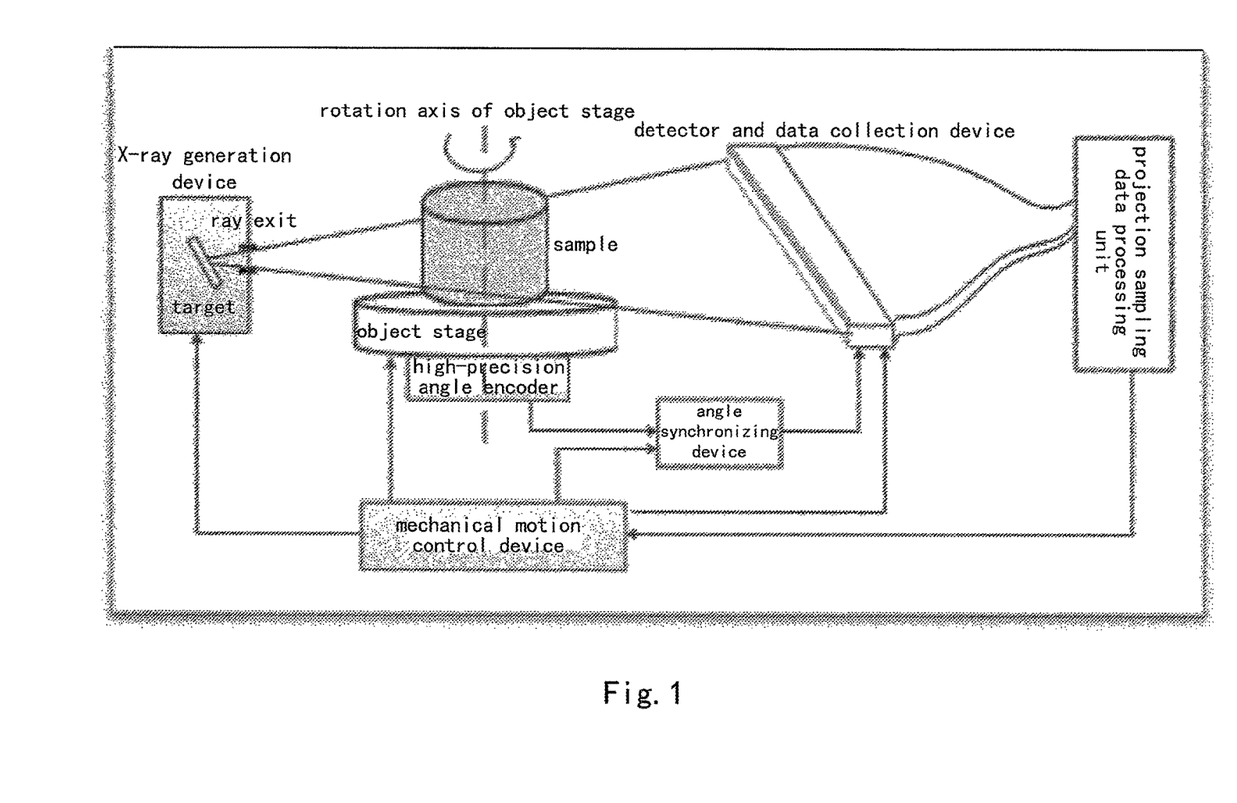
FIG. 1 is a structural representation of an X-ray CT imaging system according to an embodiment of the present invention.

As shown in FIG. 1, a CT imaging system used in the embodiments of the present invention is shown. The system includes:

an X-ray generation device including a focus target with a certain size for generating X-ray and an X-ray exit;

a mechanical motion device and a controller, wherein the mechanical motion device and the controller includes an object stage, a frame equipped with an X-ray machine and a detector, a control system, and a high-precision angle encoder; the object stage is driven in a circular orbit rotation motion and/or a linear translation motion, and the frame is driven in a linear translation motion and/or a circular orbit rotation motion, thereby achieving a circumferential scanning trajectory; in the embodiment of the present invention, a fan-beam circumferential scanning trajectory using a fixed frame and a rotatable object stage is developed as an example for description, and the high-precision angle encoder is used for achieving a precise angle positioning and a high-density angle sampling.

a data collection system including one or more rows of linear array detector units and a reading circuit, a trigger acquisition signal circuit and a data transmission circuit;

a primary control and data processing computer for controlling operation process of the CT system, including a mechanical rotation, electrical control, and safety interlocking control.

As described above, according to the method of the present invention, in a preferred embodiment, the following steps are implemented before implementing the step (1):

measuring and obtaining focus size a of an X-ray source, and measuring and obtaining a distance R between the X-ray source and a rotation center of a turntable in the X-ray CT imaging system, and determining a preset angle sampling count N according to the following formula, based on a and R:

$$N>2\pi/\tan^{-1}(a/R).$$

Using the manner described above, the number of samples exceeds the traditional CT device by an order of magnitude, thereby significantly improving the spatial resolution of the reconstructed image.

In an embodiment of the present invention, the image reconstruction method further comprises the step of: determining whether the value k exceeds the preset angle sampling count N when implementing the step (2), then, if k is greater than N, then implementing the step (3);

if k is less than N, then turning the object to be detected to next scanning angle, and continuing to implement the step (2).

In an embodiment of the present invention, the image reconstruction method further comprises the steps of:

dividing the X-ray source into a plurality of virtual sub-focuses, and determining position $a_i$ and intensity $w(a_i)$ of each virtual sub-focus;

after implementing the step (3), obtaining restoration data $p_{cir}(\beta_i,t_i)$ of the virtual sub-focuses for implementing an image reconstruction in the filtered back projection algorithm, using the following formula:

$$q(k,t) = \sum_{i=1}^{M} w(a_i) p_{cir}(\beta_i, t_i)$$

$$\begin{cases} \theta_i = \tan^{-1}(a_i/R) \\ \beta_i = k\dfrac{2\pi}{N} + \theta_i \\ t_i = D[t\cos\theta_i + (D-R)\sin\theta_i]/[R+(D-R)\cos\theta_i - t\sin\theta_i] \end{cases}$$

where D is a distance between the X-ray source and the detector, $a_i$ is a distance of one virtual sub-focus deviating from an ideal point source s, M is the number of the virtual sub-focuses, t represents position of the detector, i is a subscript of one virtual sub-focus, $\beta_i$ is projection angular position of one virtual sub-focus; and reconstructing a linear attenuation coefficient distribution image of the object to be detected by means of a filtered back projection algorithm based on the restoration data $p_{cir}(\beta_i,t_i)$.

Figure 2:
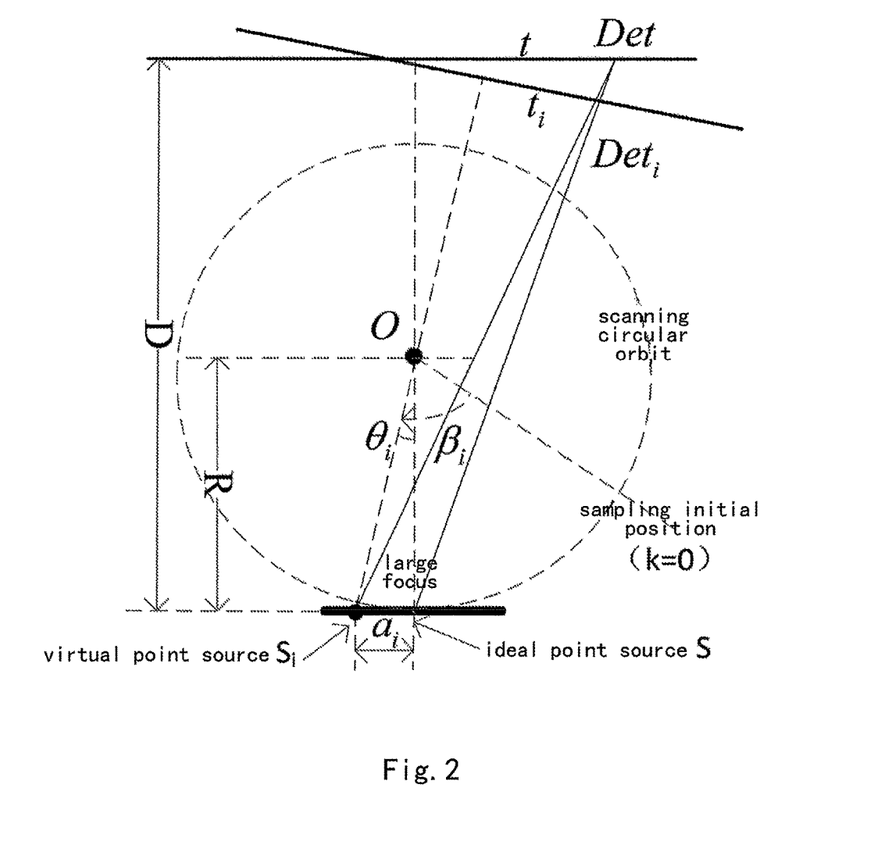
FIG. 2 is a view showing focus dividing of the method provided in the present disclosure.

According to an embodiment of the present invention, in order to improve the spatial resolution of the CT system, preferably, the focus is divided into a plurality of virtual sub-focuses, and an equivalent ideal focus (the ideal point source) is obtained based on the virtual sub-focuses, as shown in FIG. 2, which illustrate focus dividing.

The large focus of the CT imaging system is evenly divided into a plurality of virtual sub-focuses $S_i$. The projection data q(k,t) of the large focus measured by the detector unit Det at projection angle k(2π/N) may be equivalent to an accumulation of the projection data of the divided virtual sub-focuses. According to geometric relationship shown in FIG. 2, a ray path determined by the virtual sub-focus $S_i$ and the detector unit Det is identical to a ray path determined by the ideal point source at projection angle $\beta_i$ and the detector unit $Det_i$ in the case of circular orbit scanning. An angle between the projection angle $\beta_i$ and the current projection angle k(2π/N) is denoted as $\theta_i$, which is determined by the distance $a_i$ of the virtual sub-focus $S_i$ deviating from the ideal point source S and a scanning radius R of the circular orbit. Thus, the projection data q(k,t) of the large focus of the CT imaging system may be represented as a weighted sum of the projection data $p_{cir}(\beta_i,t_i)$ of the virtual sub-focuses in the case of the ideal circular orbit scanning, the weight is the intensity w($a_i$) of the virtual sub-focuses. Through the above manner, the restoration of the projection data of the virtual sub-focuses is achieved, thereby a high-resolution CT image reconstruction is achieved.

As described above, in the method provided in the present invention, the image reconstruction is implemented by the filtered back projection algorithm.

The detailed implementation steps of the reconstruction using the filtered back projection algorithm are as follows:

firstly, weighting the projection data:

$$p_{cir\_w}(\beta_i, t_i) = \frac{D}{\sqrt{D^2 + t_i^2}} p_{cir}(\beta_i, t_i)$$

then, implementing a one-dimensional ramp filtering in the direction of the detector:

$$p_{cir\_f}(\beta_i, t_i) = p_{cir\_w}(\beta_i, t_i) \otimes h(t_i)$$

$$h(nT) = \begin{cases} 1/8T^2 & n = 0 \\ 0 & n \text{ is an even number} \\ -1/2(n^2\pi^2 T^2) & n \text{ is an odd number} \end{cases}$$

where t is a sampling interval in the direction of the detector, which is typically a detector unit spacing;

implementing a weighted back projection to the filtered data (in the angular direction):

$$f(r, \phi) = \Delta\beta \sum_i \frac{1}{U^2} p_{cir\_f}(\beta_i, t_i)$$

$$U = 1 + r\sin(\beta_i - \phi)/D$$

where f(r,φ) is a polar coordinate representation of the image to be reconstructed, $$\Delta\beta = \frac{2\pi}{N}$$

is a sampling interval of the projection angle.

Figure 3:
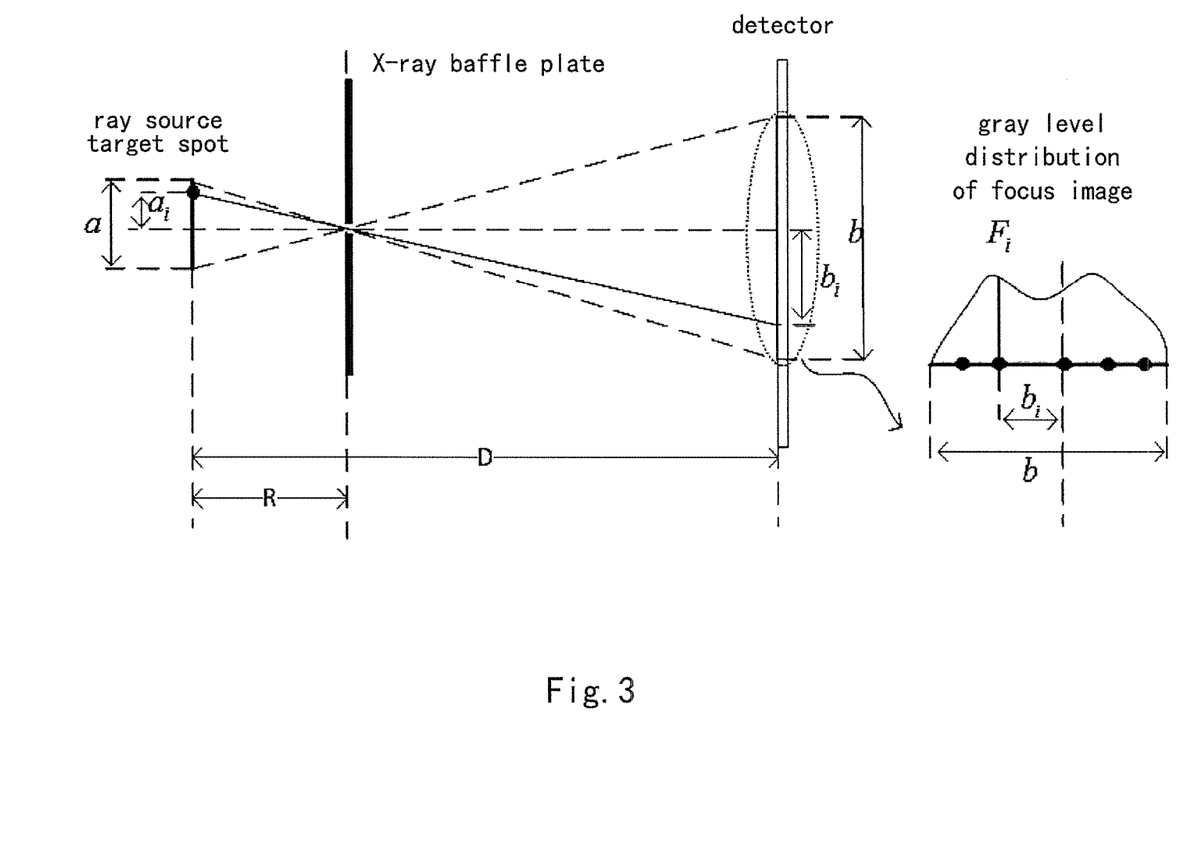
FIG. 3 is a schematic view showing determination of focus size and virtual focuses by means of a pinhole method, which is adopted by the method provided in the present disclosure.

In the present disclosure, it is possible to adopt the method illustrated in FIG. 3 to obtain the focus size, specifically, as shown in FIG. 3:

using a material with a high absorption coefficient to form a baffle plate, and making a hole thereon, then obtaining an image of the focus by means of a small hole imaging theory, thus determining the focus size a, the position $a_i$ and the intensity w($a_i$) of the virtual sub-focus through measuring gray level distribution of the focus image. Where $b_i$ is a sampling interval of the virtual sub-focus, which may typically be defined as $b_i$=b/M, where M is the number of the virtual sub-focuses, and $F_i$ is a gray value of the focus image at $b_i$.

The above-described parameters satisfy the following relationship:

$$a = \frac{b}{(D-R)} R, \quad a_i = \frac{b_i}{(D-R)} R, \quad w(a_i) = F_i \bigg/ \sum_i F_i$$

The most preferred embodiment of the present invention is given below. It should be noted that the embodiment to be described is not intended to limit the present invention, and any one of the embodiments described above can achieve the object of improving the spatial resolution in different technical routes. The most preferred embodiment below combines all the above-mentioned means to achieve the best of the technical effects. However, it does not mean to limit the present invention, that is to say, any one of the embodiments described above can resolve the problems addressed in the present invention.

In the most preferred embodiment:

The CT imaging system shown in FIG. 1 is used. In order to obtain the best spatial resolution, the image reconstruction method comprises the steps of:

(1) activating the X-ray source and the detector, implementing a focus dividing and a focus size measurement by means of the method shown in FIGS. 2 and 3, so as to obtain an intensity distribution of the focus of the system, then dividing the X-ray source into a plurality of virtual sub-focuses, for example, the large focus may be divided into 5 virtual sub-focuses, thereby determining the position $a_i$ and the intensity w($a_i$) of each virtual sub-focus;

(2) determining the angle sampling number N by means of the following formula, based on the measured focus size a and the scanning geometry parameter R:

$$N > 2\pi/\tan^{-1}(a/R)$$

(3) emitting the X-ray from the X-ray source, measuring the intensity of the ray attenuated by air, converting the intensity of the X-ray received by the detector unit at the position t into a value $I_0(t)$, and transmitting this data to the data processing computer to be stored;

(4) emitting the X-ray from the X-ray source to implement an angular scanning to the object to be detected, converting the intensity of the X-ray received by the detector unit at the position t into a value I(k,t), and transmitting this data to the data processing computer, where k is a angle sampling count with an initial value 1;

(5) if the value K is increased by 1, then determining whether the value k exceeds the preset angle sampling count N; if not, then turning the object to be detected to next scanning angle and returning back to (4), if yes, going to (6);

(6) preliminarily correcting the projection data according to the following formula, so as to obtain the attenuation coefficient q(k,t) of the X-ray received by each detector unit in different projection angles:

$$q(k,t) = -\ln [I(k,t)/I_0(t)]$$

(7) the equivalent relation between the projection data q(k,t) of the large focus obtained in the step (6) and the projection data $p_{cir}(\beta_i, t_i)$ of the equivalent sub-focuses with the same geometry scanning parameters being represented by the following formula, wherein the measured data from the different detector units in different angles form linear equations, wherein q(k,t) and w($a_i$) are known, and $p_{cir}(\beta_i, t_i)$ is unknown, the processor may achieve the restoration of the projection data $p_{cir}(\beta_i, t_i)$ of the sub-focuses by solving this linear equations $$q(k,t) = \sum_{i=1}^{M} w(a_i) p_{cir}(\beta_i, t_i)$$

-continued $$\begin{cases} \theta_i = \tan^{-1}(a_i/R) \\ \beta_i = k\dfrac{2\pi}{N} + \theta_i \\ t_i = D[t\cos\theta_i + (D-R)\sin\theta_i]/[R + (D-R)\cos\theta_i - t\sin\theta_i] \end{cases}$$

where R is a distance between the X-ray source and the rotation center O of the turntable, D is a distance between the ray source and the detector, $a_i$ is a distance of one virtual point source $S_i$ deviating from the ideal point source S, t represents position of the detector unit, i is a subscript of one virtual sub-focus.

(8) the processor reconstructs the linear attenuation coefficient distribution image of the object to be detected by means of the filtered back projection algorithm (FBP) based on the restored projection data $p_{cir}(\beta_i,t_i)$ of the sub-focuses obtained in the step (7).

According to the technical solutions of the present invention, it improves the spatial resolution of the CT system without changing the existing CT system, and it has a high efficiency of data processing and image reconstruction.

In the prior art, edges of the image are blurring and the spatial resolution is poor, only 2.4 LP/mm, in contrast, in the embodiments of the present invention, edges of the image are sharp, and the spatial resolution is much better than 3.0 LP/mm The foregoing descriptions are merely exemplary implementation manners of the present invention. The protection scope of the present invention is not limited here. Variations or replacements that may be easily thought of by persons skilled in the art without departing from the technical scope of the present invention shall fall within the protection scope of the present invention. Therefore, the protection scope of the present invention is subject to the protection scope of the claims.

What is claimed is:

1. A CT detection method, comprising the steps of:
   (1) scanning circumferentially an object to be detected by means of X-ray according to a preset angle sampling value, which represents the number of sampling points in one circle, so as to obtain a group of projection sampling data in different projection angles, the preset angle sampling value being greater than 1000;
   (2) processing the projection sampling data so as to obtain projection data of a plurality of virtual sub-focuses equivalent to a large focus of radiation source in a CT system; and
   (3) implementing an image reconstruction according to the projection data of the plurality of virtual sub-focuses;
   wherein the preset angle sampling value N is obtained according to the following formula:
   $N > 2\pi/\tan^{-1}(a/R)$, wherein a is focus size of an X-ray source, R is a distance between the X-ray source and a rotation center of the object to be detected.

2. The method according to claim 1, wherein the preset angle sampling value is greater than 8000.

3. The method according to claim 1, wherein,
   in the step (2), the projection data of the plurality of virtual sub-focuses are obtained according to the projection sampling data in different projection angles and an intensity corresponding to the plurality of virtual sub-focuses.

4. The method according to claim 3, wherein the projection data of the plurality of virtual sub-focuses are obtained using the following formula:

$$q(k,t) = \sum_{i=1}^{M} w(a_i)p_{cir}(\beta_i, t_i)$$

$$\begin{cases} \theta_i = \tan^{-1}(a_i/R) \\ \beta_i = k\dfrac{2\pi}{N} + \theta_i \\ t_i = D[t\cos\theta_i + (D-R)\sin\theta_i]/[R + (D-R)\cos\theta_i - t\sin\theta_i] \end{cases}$$

where D is a distance between the X-ray source and a detector, $a_i$ is a distance of one virtual sub-focus deviating from an ideal point source, M is the number of the virtual sub-focuses, t represents position of the detector, i is a subscript of one virtual sub-focus, $\beta_i$ is projection angular position of one virtual sub-focus, and q(k,t) is an attenuation coefficient of the X-ray, which is obtained from the following formula: $q(k,t) = -\ln [I(k,t)/I_0(t)]$.

5. The method according to claim 1, wherein,
   before the step (1), the large focus of the CT system is finely divided into the plurality of virtual sub-focuses by means of a focus size measuring method, and the intensity corresponding to the plurality of virtual sub-focuses is obtained.

6. The method according to claim 5, wherein the step of obtaining the intensity corresponding to the plurality of virtual sub-focuses comprises:
   measuring the size of the large focus of the CT system by means of a small hole imaging method;
   dividing finely the large focus into the plurality of equivalent virtual sub-focuses; and
   determining the intensity corresponding to the plurality of equivalent virtual sub-focuses according to a distribution curve of focus intensity.

7. The method according to claim 1, further comprising the step of:
   correcting the projection sampling data before the step (2).

8. The method according to claim 7, wherein the step of correcting the projection sampling data comprises:
   measuring intensity $I_0(t)$ of the ray attenuated by air;
   calculating the attenuation coefficients q(k,t) of the X-ray in different angles using the following formula:

$$q(k,t) = -\ln [I(k,t)/I_0(t)]$$

wherein k is an angle sampling count, which increases from an initial value 1 until the value k is greater than a preset angle sampling count.

9. A CT device, comprising a radiation source, a detector corresponding to the radiation source, a preset angle sampling value determining unit, a projection sampling data processing unit and a reconstruction unit, wherein,
   the preset angle sampling value determining unit is intended to determine a preset angle sampling value, which represents the number of sampling points in one circle, the preset angle sampling value being greater than 1000;
   the radiation source and the detector are disposed on either side of an object to be detected, serving as scanning circumferentially the object to be detected by means of X-ray according to the preset angle sampling value, so as to obtain a group of projection sampling data in different projection angles;

the projection sampling data processing unit is configured to process the projection sampling data so as to obtain projection data of a plurality of virtual sub-focuses equivalent to a large focus of radiation source in a CT system; and the reconstruction unit is configured to implement an image reconstruction according to the projection data of the plurality of virtual sub-focuses;

wherein the preset angle sampling value is greater than 8000, and the preset angle sampling value N is obtained according to the following formula:

$N > 2\pi/\tan^{-1}(a/R)$ wherein a is focus size of an X-ray source, R is a distance between the X-ray source and a rotation center of the object to be detected.

10. The CT device according to claim 9, wherein, the projection sampling data processing unit obtains the projection data of the plurality of virtual sub-focuses according to the projection sampling data in different projection angles and an intensity corresponding to the plurality of virtual sub-focuses, and the projection data of the plurality of virtual sub-focuses are obtained using the following formula:

$$q(k, t) = \sum_{i=1}^{M} w(a_i) p_{cir}(\beta_i, t_i)$$

$$\begin{cases} \theta_i = \tan^{-1}(a_i/R) \\ \beta_i = k\frac{2\pi}{N} + \theta_i \\ t_i = D[t\cos\theta_i + (D-R)\sin\theta_i]/[R + (D-R)\cos\theta_i - t\sin\theta_i] \end{cases}$$

where D is a distance between the X-ray source and the detector, $a_i$ is a distance of one virtual sub-focus deviating from an ideal point source, M is the number of the virtual sub-focuses, t represents position of the detector, i is a subscript of one virtual sub-focus, βi is projection angular position of one virtual sub-focus, and q(k,t) is an attenuation coefficient of the X-ray, which is obtained from the following formula: $q(k,t) = -\ln [I(k,t)/I_0(t)]$.

11. The CT device according to claim 9, further comprising a focus size measuring unit, a focus dividing unit and an intensity determining unit, wherein, the focus size measuring unit is intended to measure the size of the large focus of the CT system by means of a small hole imaging method;

the focus dividing unit is intended to divide finely the large focus into the plurality of equivalent virtual sub-focuses; and the intensity determining unit is intended to determine an intensity corresponding to the plurality of equivalent virtual sub-focuses according to a distribution curve of focus intensity.

12. The CT device according to claim 9, further comprising a data correction unit for correcting the projection sampling data, wherein, based on the measured intensity $I_0(t)$ of the ray attenuated by air, attenuation coefficients q(k,t) of the X-ray in different angles are calculated using the following formula:

$q(k,t) = -\ln [I(k,t)/I_0(t)]$, wherein k is an angle sampling count, which increases from an initial value 1 until the value k is greater than a preset angle sampling count.

13. An image reconstruction method in an X-ray CT imaging system, comprising the steps of:

(1) activating a ray generator and a detector in the X-ray CT imaging system, measuring intensity $I_0(t)$ of the ray attenuated by air at position t, and providing the measured data to a data processor in the X-ray CT imaging system;

(2) disposing an object to be detected in the X-ray CT imaging system for scanning, measuring intensity I(k,t) of the ray attenuated by the object to be detected in the current angular position at the position t, and providing the measured data to the data processor in the X-ray CT imaging system, wherein k being an angle sampling count, which increases from an initial value 1 until the value k is greater than a preset angle sampling count;

(3) calculating attenuation coefficients q(k,t) of the X-ray in different angles using the following formula (1):

$$q(k,t) = -\ln [I(k,t)/I_0(t)] \quad (1)$$

(4) reconstructing a linear attenuation coefficient distribution image of the object to be detected by means of a filtered back projection algorithm based on the data q(k,t) in the step (3).

14. The image reconstruction method according to claim 13, wherein the following steps are implemented before implementing the step (1):

measuring and obtaining focus size a of an X-ray source, and measuring and obtaining a distance R between the X-ray source and a rotation center of a turntable in the X-ray CT imaging system, and determining a preset angle sampling count N according to the following formula, based on a and R:

$N > 2\pi/\tan^-(a/R)$.

15. The image reconstruction method according to claim 14, further comprising the step of:

determining whether the value k exceeds the preset angle sampling count N when implementing the step (2), then, if k is greater than N, then implementing the step (3);

if k is less than N, then turning the object to be detected to next scanning angle, and continuing to implement the step (2).

16. The image reconstruction method according to claim 14, further comprising the steps of:

dividing the X-ray source into a plurality of virtual sub-focuses, and determining position $a_i$ and intensity $w(a_i)$ of each virtual sub-focus;

after implementing the step (3), obtaining restoration data $p_{cir}(\beta_i,t_i)$ of the virtual sub-focuses for implementing an image reconstruction in the filtered back projection algorithm, using the following formula:

$$q(k, t) = \sum_{i=1}^{M} w(a_i) p_{cir}(\beta_i, t_i)$$

$$\begin{cases} \theta_i = \tan^{-1}(a_i/R) \\ \beta_i = k\frac{2\pi}{N} + \theta_i \\ t_i = D[t\cos\theta_i + (D-R)\sin\theta_i]/[R + (D-R)\cos\theta_i - t\sin\theta_i] \end{cases}$$

where D is a distance between the X-ray source and the detector, $a_i$ is a distance of one virtual sub-focus deviating from an ideal point source s, M is the number of the virtual sub-focuses, t represents position of the detector, i is a subscript of one virtual sub-focus, βi is projection angular position of one virtual sub-focus; and reconstructing a linear attenuation coefficient distribution image of the object to be detected by means of a filtered back projection algorithm based on the restoration data $p_{cir}(\beta_i, t_i)$.

* * * * *